(12) United States Patent
Hu et al.

(10) Patent No.: US 9,857,230 B2
(45) Date of Patent: Jan. 2, 2018

(54) INFRARED DETECTOR

(71) Applicants: Tsinghua University, Beijing (CN); HON HAI PRECISION INDUSTRY CO., LTD., New Taipei (TW)

(72) Inventors: Chun-Hua Hu, Beijing (CN); Chang-Hong Liu, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 195 days.

(21) Appl. No.: 14/521,227

(22) Filed: Oct. 22, 2014

(65) Prior Publication Data

US 2015/0060769 A1    Mar. 5, 2015

Related U.S. Application Data

(62) Division of application No. 12/876,352, filed on Sep. 7, 2010.

(30) Foreign Application Priority Data

Jun. 25, 2010    (CN) .......................... 2010 1 0210121

(51) Int. Cl.
| | |
|---|---|
| *G01J 5/16* | (2006.01) |
| *G01J 5/00* | (2006.01) |
| *G01J 5/12* | (2006.01) |
| *G01J 5/14* | (2006.01) |
| *G01J 5/04* | (2006.01) |
| *B82Y 30/00* | (2011.01) |

(Continued)

(52) U.S. Cl.
CPC ................. *G01J 5/16* (2013.01); *B82Y 30/00* (2013.01); *G01J 5/023* (2013.01); *G01J 5/048* (2013.01); *G01J 5/12* (2013.01); *G01J 5/14* (2013.01); *H01L 51/0048* (2013.01); *H01L 51/441* (2013.01); *H01L 51/448* (2013.01); *G01J 1/1626* (2013.01); *G01J 5/02* (2013.01); *G01J 5/04* (2013.01); *G01J 2005/065* (2013.01); *G01J 2005/068* (2013.01); *G01N 2201/022* (2013.01); *H01L 35/32* (2013.01); *H01L 2031/0344* (2013.01)

(58) Field of Classification Search
USPC ............................................... 250/353, 338.1
See application file for complete search history.

(56) References Cited

U.S. PATENT DOCUMENTS

| | | | | |
|---|---|---|---|---|
| 4,904,090 A | * | 2/1990 | Oliver | ..................... F25B 21/04 236/94 |
| 4,927,246 A | * | 5/1990 | Ito | ......................... G02F 1/1523 359/275 |

(Continued)

*Primary Examiner* — David Porta
*Assistant Examiner* — Carolyn Igyarto
(74) *Attorney, Agent, or Firm* — ScienBiziP, P.C.

(57) ABSTRACT

An infrared detector based on carbon nanotubes is provided. The infrared detector includes a detecting element, a first electrode and a second electrode. The detecting element includes an absorbing part and a non-absorbing part. A first end is located in the absorbing part. A second end is located in the non-absorbing part. An angle between the absorbing part and the non-absorbing part is less than 90 degrees. A first electrode is electrically connected with the first end. A second electrode is electrically connected with the second end.

13 Claims, 13 Drawing Sheets

(51) Int. Cl.
  *H01L 51/00*     (2006.01)
  *H01L 51/44*     (2006.01)
  *H01L 31/0256*   (2006.01)
  *G01J 5/02*      (2006.01)
  *H01L 35/32*     (2006.01)
  *G01J 5/06*      (2006.01)
  *G01J 1/16*      (2006.01)

(56) References Cited

U.S. PATENT DOCUMENTS

| | | | |
|---|---|---|---|
| 8,110,883 B2 * | 2/2012 | Ward | G01J 5/02 |
| | | | 257/428 |
| 2005/0133721 A1 * | 6/2005 | Kim | G01J 5/02 |
| | | | 250/338.1 |
| 2009/0075545 A1 * | 3/2009 | Lashmore | B29C 55/00 |
| | | | 442/329 |
| 2012/0003813 A1 * | 1/2012 | Chuang | H01L 21/0206 |
| | | | 438/458 |

* cited by examiner

FIG. 13

INFRARED DETECTOR

RELATED APPLICATIONS

This application is a continuation application of U.S. patent application Ser. No. 12/876,352, filed on Sep. 7, 2010, entitled "INFRARED DETECTOR," which claims all benefits accruing under 35 U.S.C. §119 from China Patent Applications: Application No. 201010210121.0, filed on Jun. 25, 2010 in the China Intellectual Property Office, the contents of which are hereby incorporated by reference.

BACKGROUND

1. Technical Field

The present disclosure generally relates to infrared detectors.

2. Description of Related Art

Infrared detectors are used to detect infrared which are not visible to humans. Infrared detectors are used in the medical field, mine detecting field, military affairs, and everyday life.

Infrared detectors can be divided into active infrared detectors and passive infrared detectors according to their working principles and structures. An active infrared detector includes an infrared producing device, an infrared receiving device, and a warning device. When humans, animals or other things pass through the infrared produced by the infrared producing device, the energy of the infrared will change, and the infrared receive device can detect a change of the energy and activate the warning device. Passive infrared detectors do not produce infrared. Instead, the passive infrared detector detects the energy of the infrared signals when infrared irradiates the device. An infrared detector, whether active or passive, should include a detecting element sensitive to infrared. The conventional detecting element uses the photoelectric effect to change infrared into electric signals, and the infrared signals are detected by detecting the electric signals. However, due to the low efficiency of the photoelectric effect, the infrared detected must have enough intensity. As such, the conventional infrared detectors have low sensitivity.

What is needed, therefore, is an infrared detector based on carbon nanotubes that can overcome the above-described shortcomings.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 2:
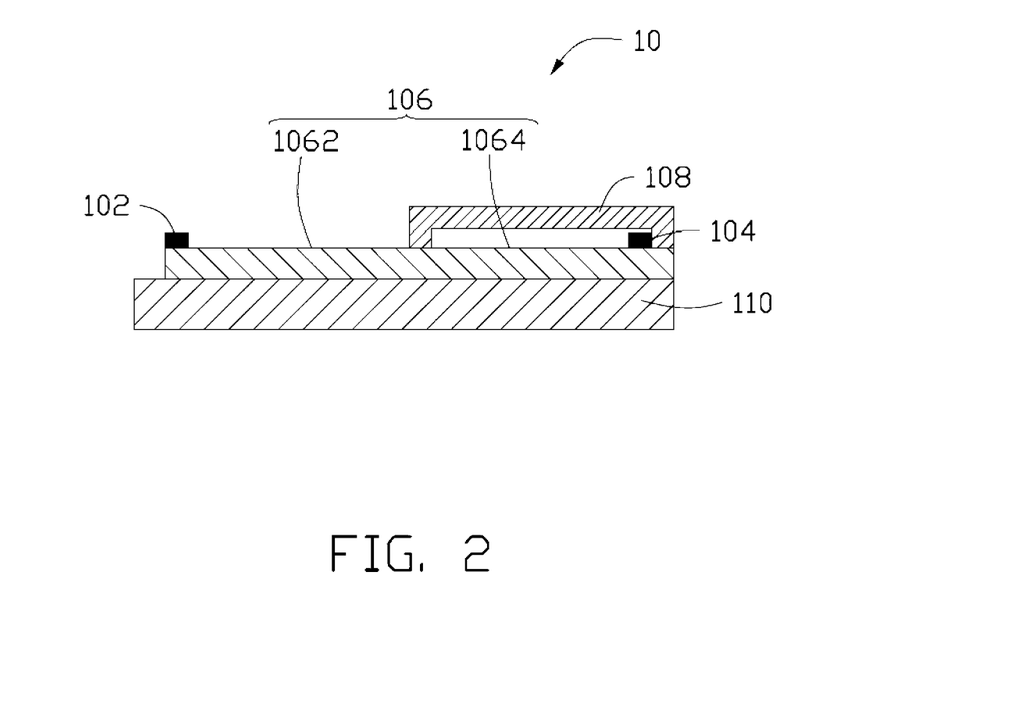
FIG. 2 is a schematic, section view along II-II of an embodiment of the infrared detector in FIG. 1.

Referring to FIG. 2, an infrared detector 10 of one embodiment includes a first electrode 102, a second electrode 104, a detecting element 106, and a covering structure 108. The first electrode 102 and the second electrode 104 are disposed on two opposite ends of the detecting element 106 and are electrically connected with the detecting element 106. The covering structure 108 covers part of the detecting element 106. The infrared detector 10 further includes a substrate 110, with the detecting element 106 disposed on a surface of the substrate 110.

The substrate 110 is used to support the detecting element 106. If the detecting element 106 is self-standing, the substrate 110 can be omitted. A material of the substrate 110 can be dielectric materials, such as glass, ceramic, polymer, and wood. The substrate 110 can also be made of conductive materials coated with dielectric materials. In this embodiment, the substrate 110 does not absorb infrared or absorbs little infrared. A thickness of the substrate 110 can be in a range from about 1 millimeter to about 2 centimeters. In one embodiment according to FIG. 1, the substrate 110 is a square ceramic sheet of about 5 millimeters thick.

The detecting element 106 is divided into an absorbing part 1062 and a non-absorbing part 1064. The covering structure 108 covers the non-absorbing part 1064. The absorbing part 1062 is used to absorb infrared irradiating on the infrared detector 10. The non-absorbing part 1064 should not absorb the infrared. A temperature of the absorbing part 1062 increases after absorbing the infrared. Thus, a temperature difference exists between the absorbing part 1062 and the non-absorbing part 1064. A material of the detecting element 106 should have a high thermoelectric transfer coefficient. The detecting element 106 has a planar structure. The planar structure can be a porous planar structure, such as a net structure. The detecting element 106 can be a carbon nanotube layer. The carbon nanotube layer can be planar or convex. The carbon nanotube layer can be a freestanding structure, that is, the carbon nanotube layer can be supported by itself without a substrate. For example, if at least one point of the carbon nanotube layer is held, the entire carbon nanotube layer can be lifted without being destroyed. The carbon nanotube layer includes a number of carbon nanotubes disposed uniformly and joined by Van der Waals attractive force therebetween. The carbon nanotubes can be single-walled carbon nanotubes, double-walled carbon nanotubes, multi-walled carbon nanotubes, or combination thereof. In this embodiment, the carbon nanotubes are single-walled carbon nanotubes. The carbon nanotube layer can be a substantially pure structure of carbon nanotubes, with few impurities. The carbon nanotubes can be used to form many different structures and provide a large specific surface area. The heat capacity per unit area of the carbon nanotube layer can be less than about $2\times10^{-4}$ J/m$^2$*K. In one embodiment, the heat capacity per unit area of the carbon nanotube layer is less than or equal to about $1.7\times10^{-6}$ J/m$^2$*K.

The carbon nanotubes in the carbon nanotube layer can be orderly or disorderly arranged. The term 'disordered carbon nanotube layer' refers to a structure where the carbon nanotubes are arranged along different directions, and the aligning directions of the carbon nanotubes are random. The number of the carbon nanotubes arranged along each different direction can be almost the same (e.g. uniformly disordered). The disordered carbon nanotube layer can be isotropic, namely the carbon nanotube layer has properties identical in all directions of the carbon nanotube layer. The carbon nanotubes in the disordered carbon nanotube layer can be entangled with each other.

The term 'ordered carbon nanotube layer' refers to a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions). The carbon nanotubes in the carbon nanotube layer can be single-walled, double-walled, and/or multi-walled carbon nanotubes. In this embodiment, the carbon nanotube layer is a substantially pure structure of single-walled carbon nanotubes.

The carbon nanotube layer can be a film structure with a thickness ranging from about 100 nanometers (nm) to about 5 mm. The carbon nanotube layer can include at least one carbon nanotube film.

In one embodiment, the carbon nanotube film is a drawn carbon nanotube film. A film can be drawn from a carbon nanotube array to obtain a drawn carbon nanotube film. The drawn carbon nanotube film includes a number of successive and oriented carbon nanotubes joined end-to-end by Van der Waals attractive force therebetween. The drawn carbon nanotube film is a free-standing film. Each drawn carbon nanotube film includes a number of successively oriented carbon nanotube segments joined end-to-end by Van der Waals attractive force therebetween. Each carbon nanotube segment includes a number of carbon nanotubes substantially parallel to each other, and joined by Van der Waals attractive force therebetween. Some variations can occur in the drawn carbon nanotube film. The carbon nanotubes in the drawn carbon nanotube film are oriented along a preferred orientation. The carbon nanotube film can be treated with an organic solvent to increase the mechanical strength and toughness of the carbon nanotube film and reduce the coefficient of friction of the carbon nanotube film. The thickness of the carbon nanotube film can range from about 0.5 nm to about 100 μm.

The carbon nanotube layer of the detecting element 106 can include at least two stacked carbon nanotube films. In other embodiments, the carbon nanotube layer can include two or more coplanar carbon nanotube films, and can include layers of coplanar carbon nanotube films. Additionally, if the carbon nanotubes in the carbon nanotube film are aligned along one preferred orientation (e.g., the drawn carbon nanotube film), an angle can exist between the orientations of the carbon nanotubes in adjacent films, whether stacked or adjacent. Adjacent carbon nanotube films can be joined only by the Van der Waals attractive force therebetween. The number of the layers of the carbon nanotube films is not limited. The thicker the carbon nanotube layer, the smaller the specific surface area. An angle between the aligned directions of the carbon nanotubes in two adjacent carbon nanotube films can range from about 0 degrees to about 90 degrees. If the angle between the aligned directions of the carbon nanotubes in adjacent carbon nanotube films is larger than 0 degrees, the carbon nanotubes in the detecting element 106 define a microporous structure. The carbon nanotube layer in an embodiment employing these films will have a number of micropores. Stacking the carbon nanotube films will also add to the structural integrity of the carbon nanotube layer.

In other embodiments, the carbon nanotube film can be a flocculated carbon nanotube film. The flocculated carbon nanotube film can include a number of long, curved, disordered carbon nanotubes entangled with each other. Furthermore, the flocculated carbon nanotube film can be isotropic. The carbon nanotubes can be substantially uniformly dispersed in the carbon nanotube film. Adjacent carbon nanotubes are acted upon by Van der Waals attractive force to obtain an entangled structure with micropores defined therein. It is noteworthy that the flocculated carbon nanotube film is very porous. Sizes of the micropores can be less than about 10 μm. The porous nature of the flocculated carbon nanotube film will increase the specific surface area of the carbon nanotube layer. Further, due to the carbon nanotubes in the carbon nanotube layer being entangled with each other, the carbon nanotube layer employing the flocculated carbon nanotube film has excellent durability, and can be fashioned into desired shapes with a low risk to the integrity of the carbon nanotube layer. The thickness of the flocculated carbon nanotube film can range from about 0.5 nm to about 1 mm.

In other embodiments, the carbon nanotube film can be a pressed carbon nanotube film. The pressed carbon nanotube film can be a free-standing carbon nanotube film. The carbon nanotubes in the pressed carbon nanotube film are arranged along a same direction or along different directions. The carbon nanotubes in the pressed carbon nanotube film can rest upon each other. Adjacent carbon nanotubes are attracted to each other and are joined by Van der Waals attractive force. An angle between a primary alignment direction of the carbon nanotubes and a surface of the pressed carbon nanotube film is about 0 degrees to approximately 15 degrees. The greater the pressure applied, the smaller the angle obtained. If the carbon nanotubes in the pressed carbon nanotube film are arranged along different directions, the carbon nanotube layer can be isotropic. Here, "isotropic" means the carbon nanotube film has properties identical in all directions substantially parallel to a surface of the carbon nanotube film. The thickness of the pressed carbon nanotube film ranges from about 0.5 nm to about 1 mm.

Because the heat capacity of the carbon nanotube layer is very low, the temperature of the detecting element 106 can rise and fall quickly, and has a high heating speed response. Further, because the carbon nanotube has a large specific surface area, the carbon nanotube layer with a number of carbon nanotubes has a larger specific surface area and a high infrared absorbing efficiency.

The first electrode 102 and the second electrode 104 can be separately disposed on two opposite ends of the detecting element 106. The detecting element 106 includes a first end (not labeled) and a second end (not labeled) opposite with the first end. The first end is in the absorbing part 1062, the second end is in the non-absorbing part 1064. The first electrode 102 is electrically connected with the first end, and the second electrode 104 is electrically connected with the second end. The first electrode 102 is disposed on the absorbing part 1062, and the second electrode 104 is disposed on the non-absorbing part 1064. The first electrode 102 and the second electrode 104 are made of conductive material. The shapes of the first electrode 102 and the second electrode 104 can be wire-shaped or bar-shaped. The cross sectional shape of the first electrode 102 and the second electrode 104 can be round, square, trapezium, triangular, or polygonal. The thickness of the first electrode 102 and the second electrode 104 can be any size, depending on the design, and can be about 1 micrometer to about 5 millimeters. In one embodiment, if the detecting element 106 includes the carbon nanotube layer having a number of carbon nanotubes arranged in a same direction, the axes of the carbon nanotubes can be substantially perpendicular to the first electrode 102 and the second electrode 104. A material of the first electrode 102 and the second electrode 104 can be metal, conductive polymer, or ITO.

The covering structure 108 is configured to cover the non-absorbing part 1064, so that the infrared cannot be absorbed by the non-absorbing part 1064. The material of the covering structure 108 can be conductive or insulated. The electrically conductive material can be metal or alloy. The metal can be copper, aluminum, or titanium. The insulated material can be resin, ceramic, plastic, or wood. The thickness of the covering structure 108 can range from about 0.5 μm to about 2 mm. If the material of the covering structure 108 is insulated, the covering structure 108 can be directly disposed on a surface of the detecting element 106. If the covering structure 108 is conductive, the covering structure 108 should be insulated from the detecting element 106. The covering structure 108 can be disposed above the detecting element 106 and apart from the detecting element 106.

The absorbing part 1062 and the non-absorbing part 1064 are two different parts of the detecting element 106 divided by the covering structure 108. In the working state of the infrared detector 10, the absorbing part 1062 absorbs infrared, and the non-absorbing part 1064 is insulated from the infrared. In one embodiment according to FIG. 2, the absorbing part 1062 is not covered by the covering structure 108 and is able to absorb infrared when the infrared irradiates on the infrared detector 10. The non-absorbing part 1064 is covered by the covering structure 108 and is not able to absorb infrared when the infrared irradiates on the infrared detector 10. An area ratio between the absorbing part 1062 and the non-absorbing part 1064 can be in a range from about 1:2 to about 2:1. In one embodiment, the area ratio between the absorbing part 1062 and the non-absorbing part 1064 is about 3:2.

The infrared detector 10 can further include a first lead wire (not shown) and a second lead wire (not shown). The first lead wire is electrically connected with the first electrode 102, and the second lead wire is electrically connected with the second electrode 104. The first lead wire can facilitate the first electrode 102 electrically connected with a power source the second lead wire can facilitate the second electrode 104 electrically connected with the power source.

Figure 1:
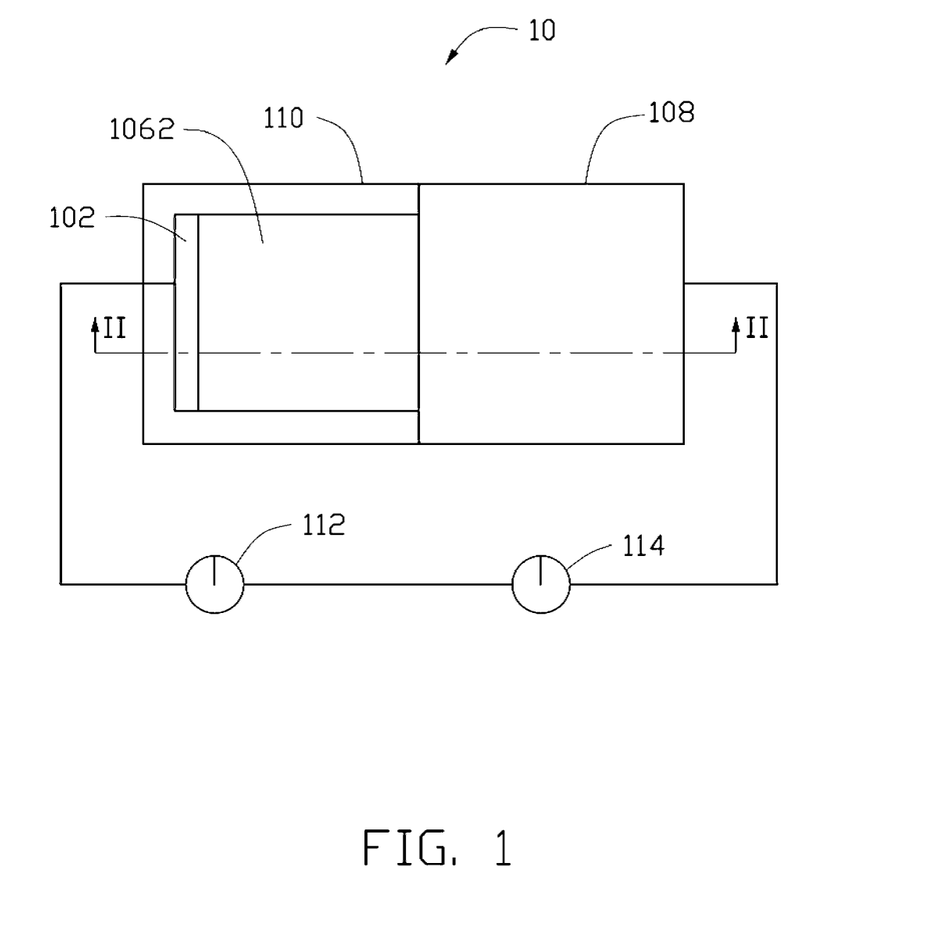
FIG. 1 is a schematic view of one embodiment of an infrared detector.

The infrared detector 10 can further include an ammeter 112 and a voltmeter 114. The ammeter 112 and the voltmeter 114 are connected in series with the first electrode 102 and the second electrode 104. The voltmeter 114 is configured to test the voltage between the first electrode 102 and the second electrode 104. The ammeter 112 is configured to test the electric current of the return circuit composed of the first electrode 102, the second electrode 104, and the detecting element 106.

Figure 3:
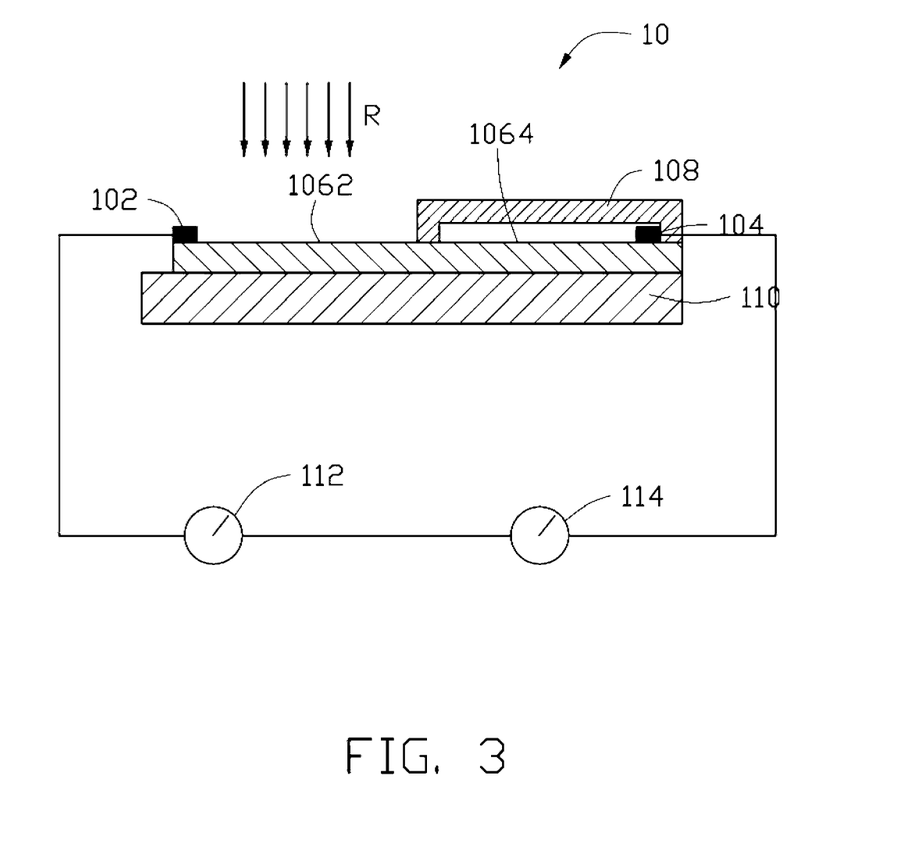
FIG. 3 is a schematic view of the infrared detector of FIG. 1 in a working state.

Referring to FIG. 3, the working principle of the infrared detector 10 is described here. When the infrared R is irradiating on the infrared detector 10, the absorbing part 1062 of the detecting element 106 absorbs the infrared R, and a temperature of the absorbing part 1062 increases. However, the non-absorbing part 1064 is covered by the covering structure 108 and cannot absorb the infrared. As such, there is a temperature difference between the first end and the second end of the detecting element 106. Because of a thermoelectric effect, a voltage difference exists between the first electrode 102 and the second electrode 104. The value of the voltage is related to the intensity of the infrared R. As such, the infrared detector can detect the infrared R and the intensity of the infrared R.

Figure 4:
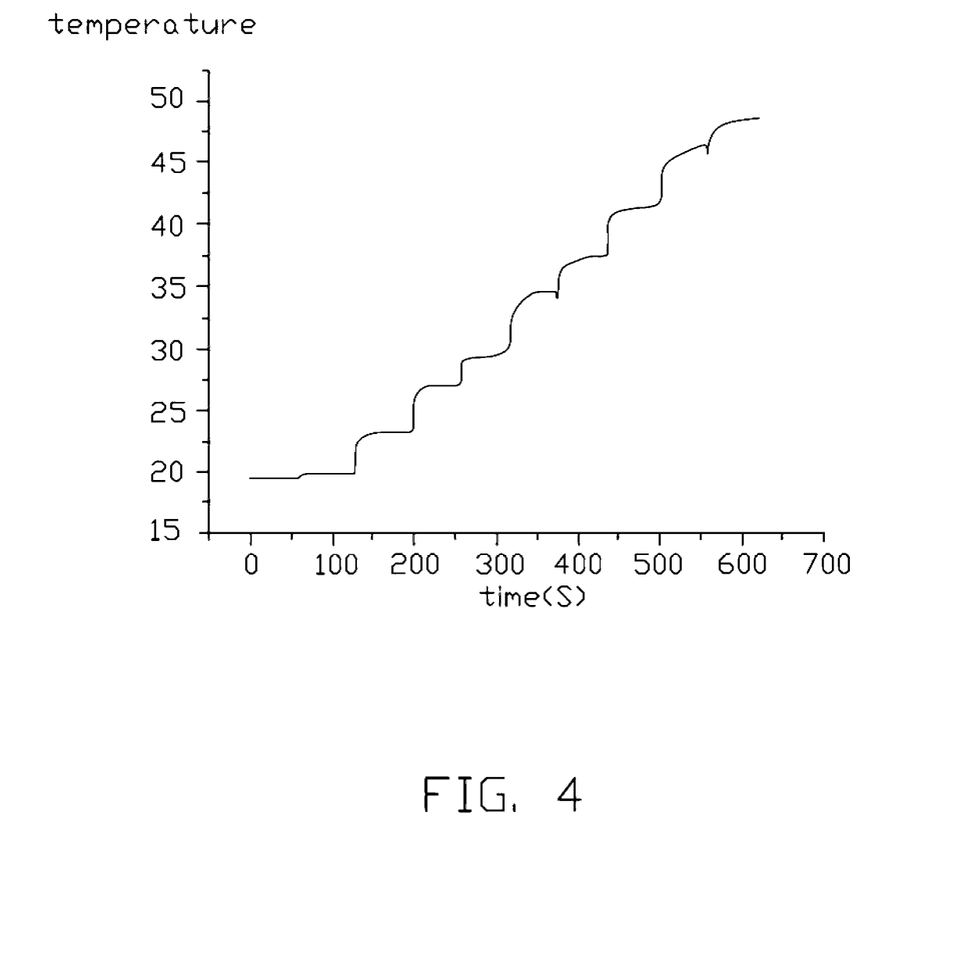
FIG. 4 is a chart showing the relationship between the irradiating area temperature and the infrared irradiating time.
Figure 5:
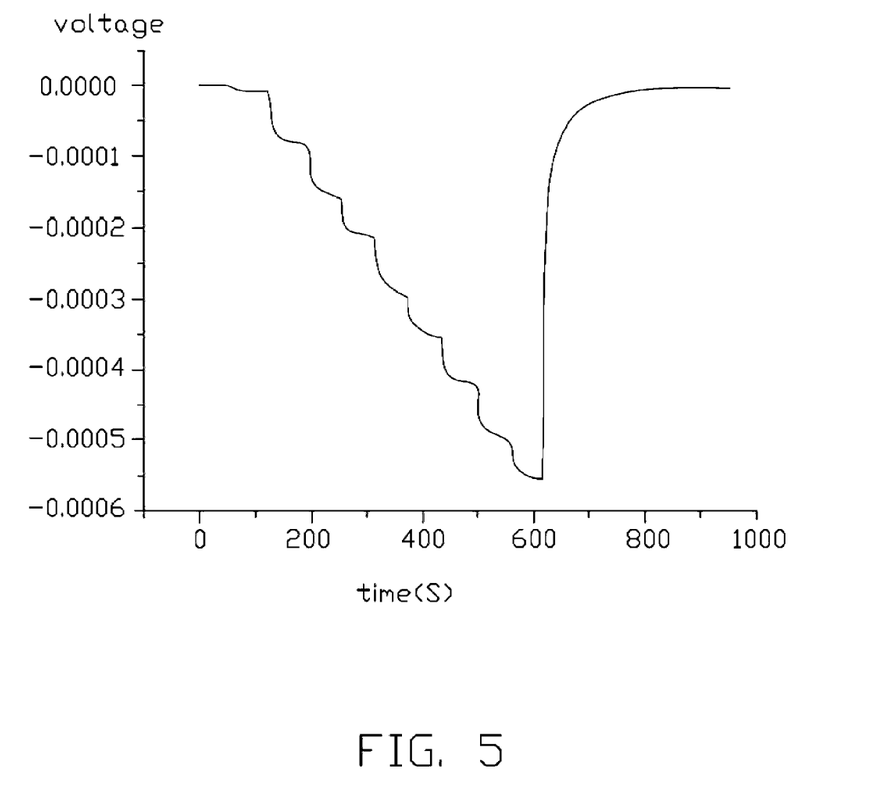
FIG. 5 is a chart showing the relationship between a voltage between the first electrode and the second electrode and the infrared irradiating time.

Referring to FIG. 4, the infrared detector 10 is alternatively exposed to ten different infrared energy densities for about 100 seconds each. The energy densities are 5.709 mW/cm$^2$, 25.394 mW/cm$^2$, 45.079 mW/cm$^2$, 64.764 mW/cm$^2$, 84.449 mW/cm$^2$, 104.134 mW/cm$^2$, 123.819 mW/cm$^2$, 143.504 mW/cm$^2$, 163.189 mW/cm$^2$. In addition, the temperature of the first end 1066 of the detecting element 106 changes quickly according to the infrared energy density. FIG. 5 shows the voltage differences between the first electrode 102 and the second electrode 104 from the ten different infrared energy densities. When the energy density of the infrared changes, the voltage difference between the first electrode 102 and the second electrode 104 changes quickly and accordingly. A relative large voltage difference between the first electrode 102 and the second electrode 104 can be produced under low infrared energy density. As such, the infrared detector 10 has a high sensitivity.

The infrared detector 10 disclosed above has numerous advantages. Firstly, the infrared detector 10 changes the infrared energy into an electrical signal based on the thermoelectric effect. Infrared with low energy density can be detected. Even low energy density infrared can cause a temperature difference between the first end and the second end. Thus, the infrared detector 10 has high sensitivity. Secondly, because the detecting element 106 includes a carbon nanotube layer, and carbon nanotubes are ideal black bodies, the detecting element 106 has high infrared absorbing efficiency, and accordingly the infrared detector 10 has high infrared absorbing efficiency. Lastly, the carbon nanotube layer, especially a carbon nanotube layer having a pure structure of single-walled carbon nanotubes, has high thermoelectric conversion efficiency, and therefore, the detecting element 106 can detect infrared with low energy density.

Figure 6:
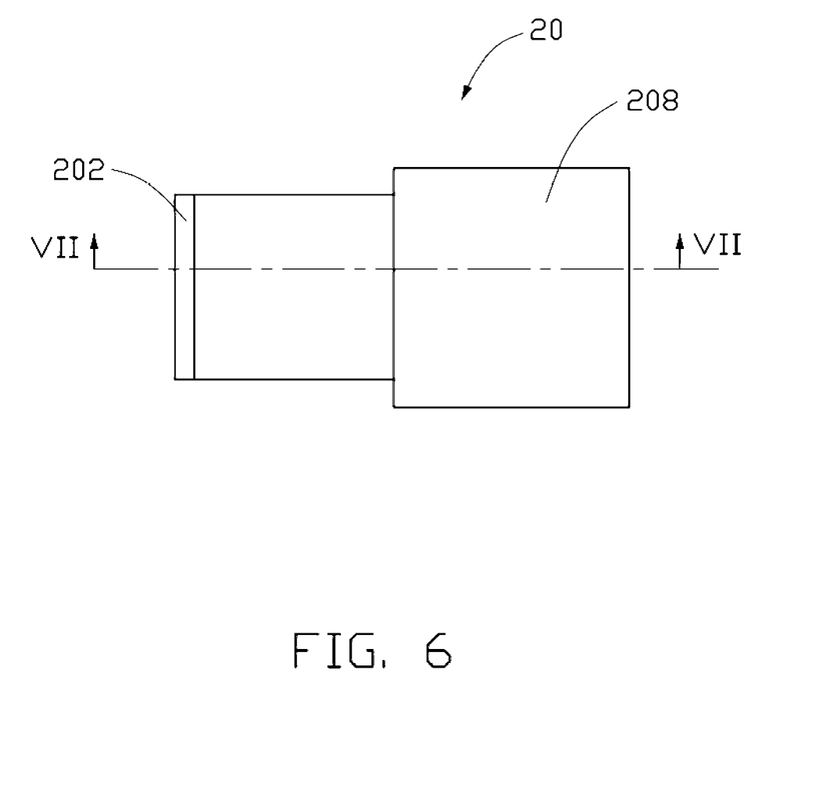
FIG. 6 is a schematic view of another embodiment of an infrared detector.
Figure 7:
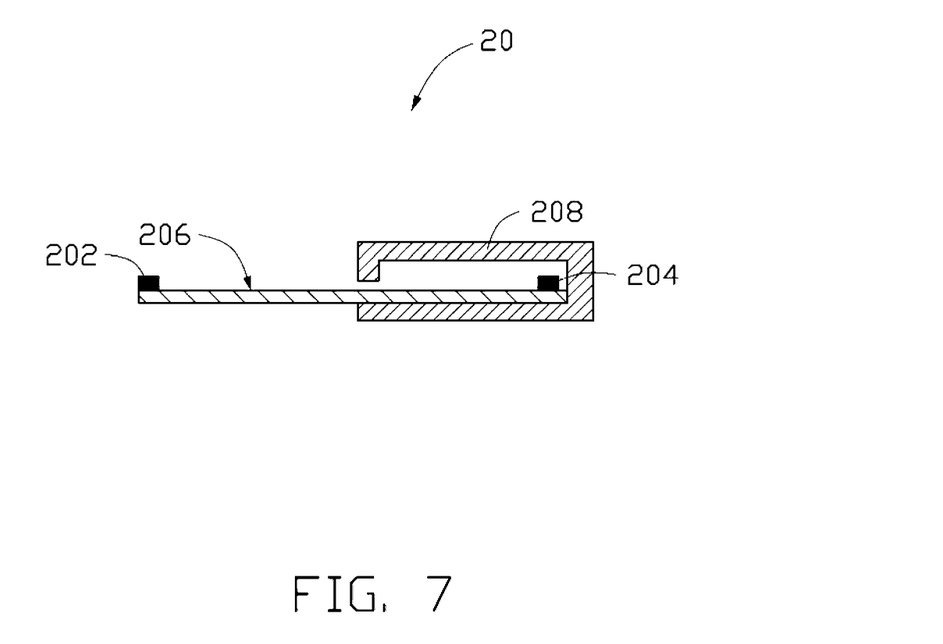
FIG. 7 is a schematic, section view along VII-VII of the infrared detector in FIG. 6.

Referring to FIGS. 6 and 7, an infrared detector 20 another embodiment includes a first electrode 202, a second electrode 204, a detecting element 206, and a covering structure 208. The first electrode 202 and the second electrode 204 are disposed on opposite ends of the detecting element 206 and are electrically connected with the detecting element 206. The covering structure 208 covers part of the detecting element 206.

The covering structure 208 is a U-shaped frame including a first covering sheet and a second covering sheet substantially parallel with each other. The first covering sheet and the second covering sheet define a hollow space. Part of the detecting element 206 is disposed on a surface of the second covering sheet and in the hollow space. Another part of the detecting element 206 is located outside of the covering structure 208. The first covering sheet covers the part disposed in the hollow space, and is a non-absorbing part (not labeled). The other part outside of the covering structure 208 is an absorbing part (not labeled). The absorbing part absorbs infrared, and the non-absorbing part is insulated from the infrared.

Other characteristics of the infrared detector 20 are the same as the infrared detector 10 disclosed above.

Figure 8:
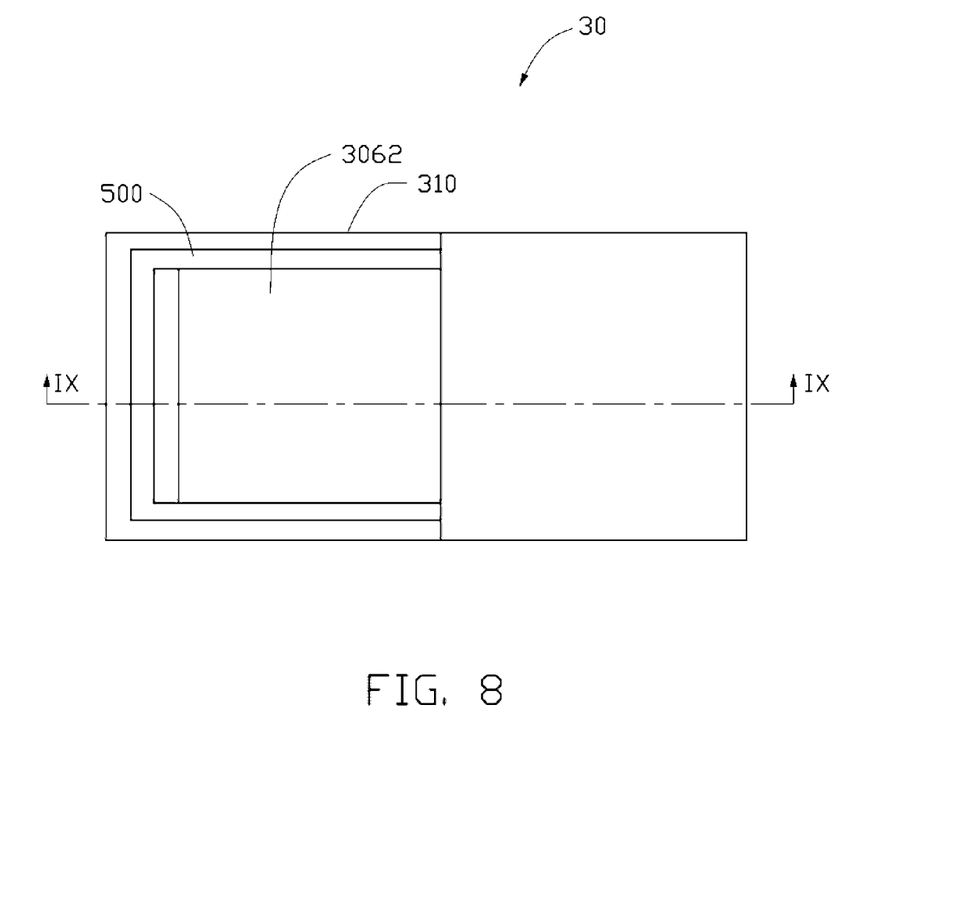
FIG. 8 is a schematic view of yet another embodiment of an infrared detector.
Figure 9:
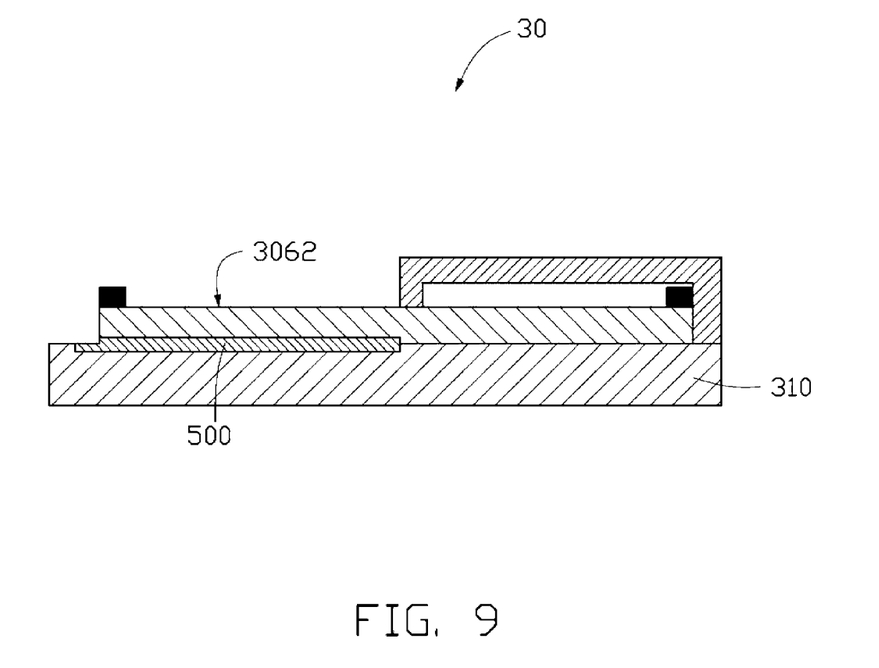
FIG. 9 is a schematic, section view along IX-IX of the infrared detector in FIG. 8.

Referring to FIGS. 8 and 9, an infrared detector 30 according to still another embodiment includes a reflective layer 500 disposed between the absorbing part 3062 and the substrate 310. The reflective layer 500 is configured to reflect the heat of the absorbing part 3062 and infrared irradiating on the substrate 310, so that the absorbing part 3062 has a high absorbing efficiency. A material of the reflective layer 500 can be insulative materials. The insulative materials can be metal oxides, metal salts, or ceramics. The reflective layer 500 can also be IR-reflective material, such as $TiO_2$—Ag—$TiO_2$, ZnS—Ag—ZnS, AlNO—Ag—AlN, $Ta_2O_3$—SiO or $Nb_2O_3$—$SiO_2$. A thickness of the reflective layer 500 can be in a range from about 20 micrometers to about 500 micrometers.

Other characteristics of the infrared detector 30 are the same as the infrared detector 10 disclosed above.

Figure 10:
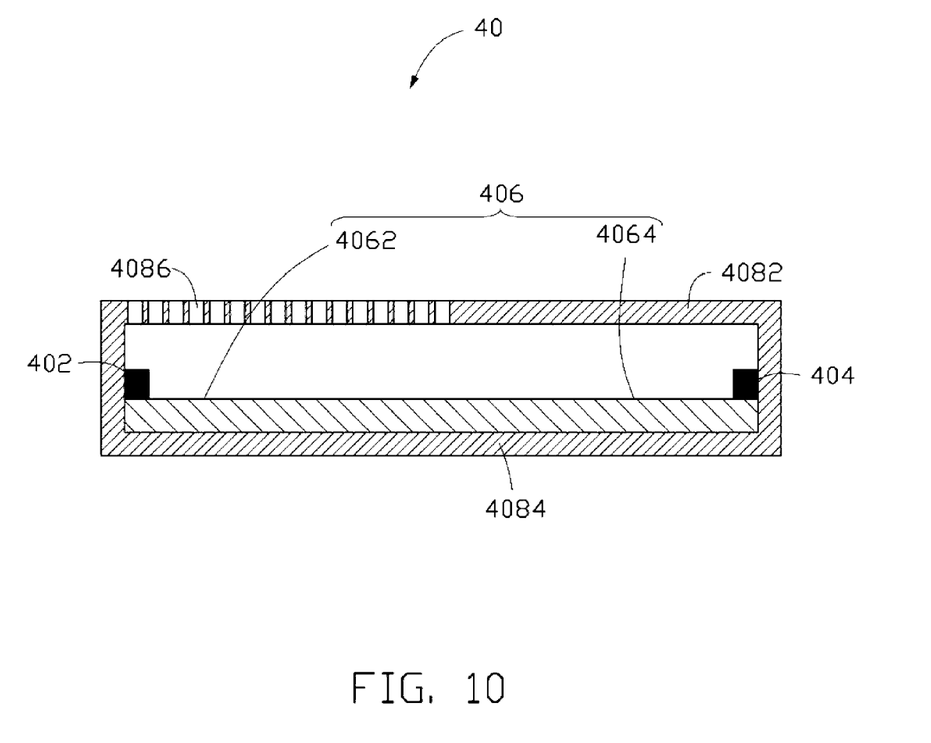
FIG. 10 is a schematic side section view of still another embodiment of an infrared detector.
Figure 11:
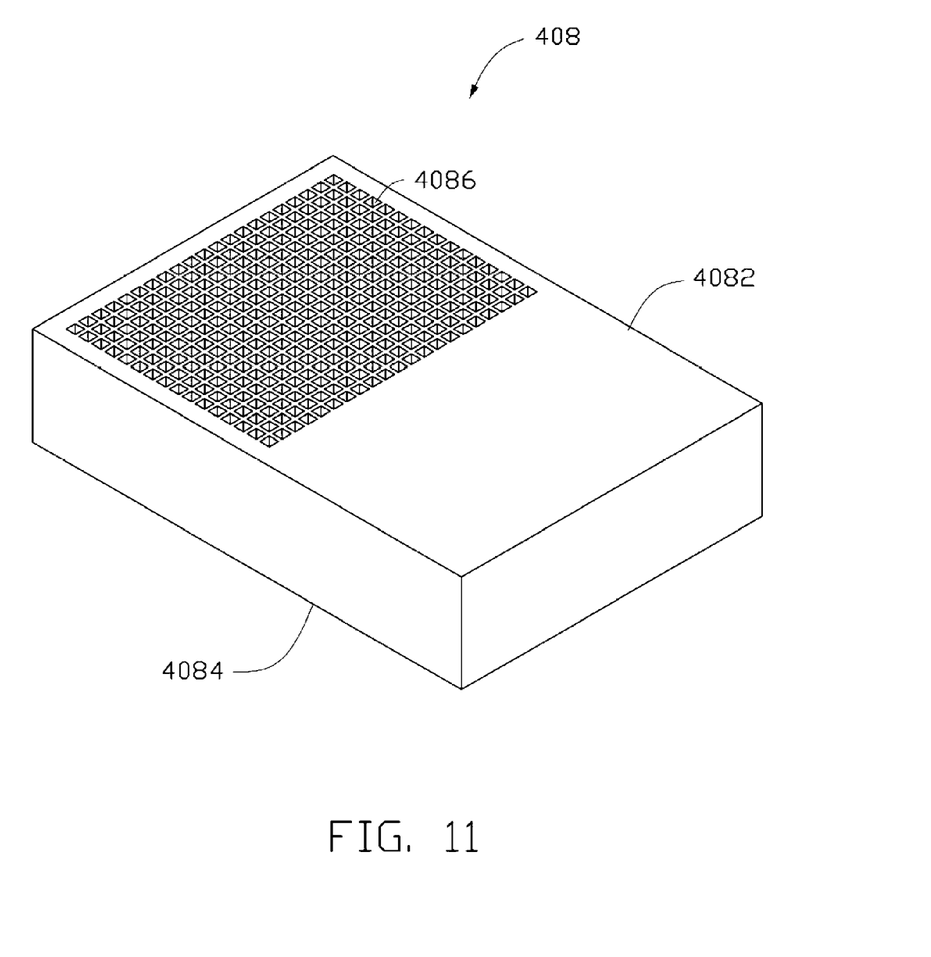
FIG. 11 is a schematic view of the covering structure of the infrared detector in FIG. 10.

Referring to FIGS. 10 and 11, an infrared detector 40 according to yet another embodiment includes a first electrode 402, a second electrode 404, a detecting element 406 and a covering structure 408. The first electrode 402 and the second electrode 404 are disposed on opposite ends of the detecting element 406 and are electrically connected with the detecting element 406. The covering structure 408 covers part of the detecting element 406. The detecting element 406 includes an absorbing part 4062 and a non-absorbing part 4064.

The covering structure 408 is an enclosure defining a hollow space, the detecting element 406 is disposed in the covering structure 408. The covering structure 408 includes a light-passing region 4086. The absorbing part 4062 of the detecting element 406 opposes the light-passing region 4086. The infrared can pass through the light-passing region 4086 and irradiate the absorbing part 4062. The light-passing region 4086 can define a number of through holes. Alternatively, the light-passing region 4086 can be transparent. A shape of the covering structure 408 is not limited, and can be cylindrical, cubical, or spherical. In one embodiment according to FIGS. 10 and 11, the covering structure 408 has a cube structure. The covering structure 408 includes an upper sheet 4082, a lower sheet 4084, and four side sheets (not labeled). The detecting element 406 is disposed on a surface of the lower sheet 4084. The light-passing region 4086 is defined on the upper sheet 4082 and includes a number of through holes. The light-passing region 4086 has a net structure.

Other characteristics of the infrared detector 40 are the same as the infrared detector 10 disclosed above.

Figure 12:
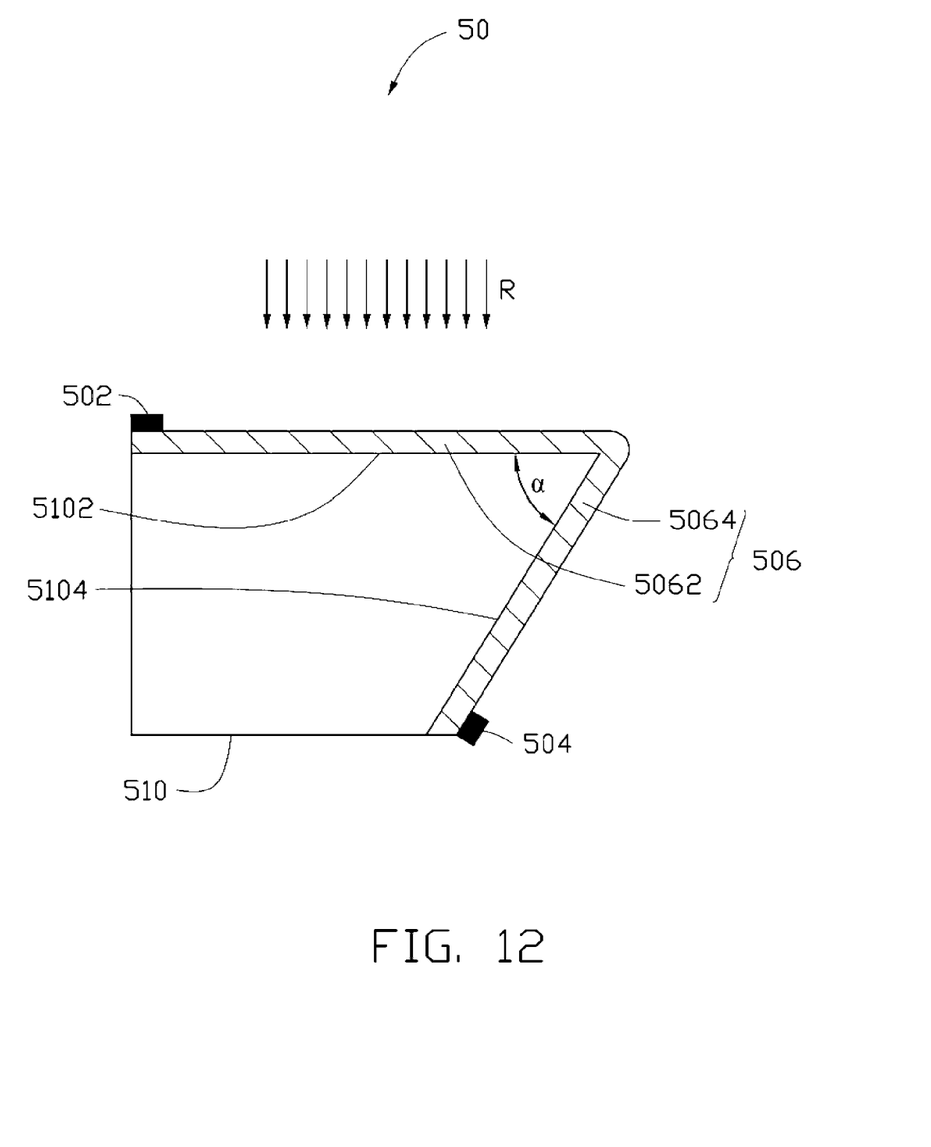
FIG. 12 is a schematic view of still yet another embodiment of an infrared detector.

Referring to FIG. 12, an infrared detector 50 according to yet another embodiment includes a first electrode 502, a second electrode 504, and a detecting element 506. The first electrode 502 and the second electrode 504 are disposed on opposite ends of the detecting element 506 and are electrically connected with the detecting element 506. The detecting element 506 includes an absorbing part 5062 and a non-absorbing part 5064.

The infrared detector 50 further includes an insulated structure 510. The insulated structure 510 includes a first surface 5102 and a second surface 5104. An angle α existing between the first surface 5102 and the second surface 5104 is less than 90 degrees. The first surface 5102 and the second surface 5104 can be two opposite surfaces of the insulated structure 510. The absorbing part 5062 is disposed on the first surface 5102, and the non-absorbing part 5064 is disposed on the second surface 5104. As such, the detecting element 506 is curved, and an angle between the absorbing part 5062 and the non-absorbing part 5064 is less than 90 degrees. In the embodiment shown in FIG. 12, the detecting element 506 is curved along its entire length and contains an angle between the absorbing part 5062 and the non-absorbing part 5064. When an infrared R is irradiating on the absorbing part 5062, the non-absorbing part 5064 cannot be irradiated by the infrared R because the angle between the absorbing part 5062 and the non-absorbing part 5064 is less than 90 degrees.

Other characteristics of the infrared detector 50 are the same as the infrared detector 10 disclosed above.

Figure 13:
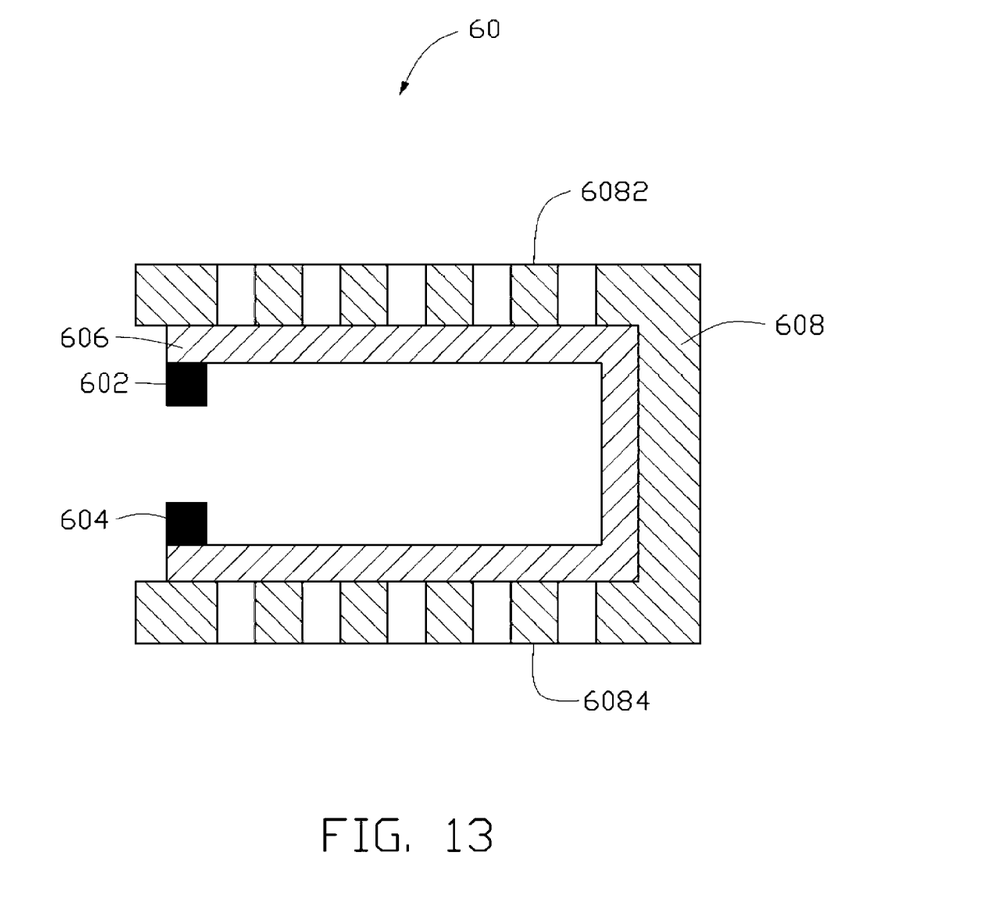
FIG. 13 is a schematic view of one embodiment of an infrared detector.

Referring to FIG. 13, an infrared detector 60 according to still yet another embodiment includes a first electrode 602, a second electrode 604, a detecting element 606, and a covering structure 608. The first electrode 602 and the second electrode 604 are disposed on two opposite ends of the detecting element 606 and are electrically connected with the detecting element 606. The covering structure 608 covers part of the detecting element 606.

The covering structure 608 is an enclosure defining a hollow space, and the detecting element 606 is disposed in the covering structure 608. The covering structure 608 includes an upper sheet 6082 and a lower sheet 6084 opposite to the upper sheet 6082. The upper sheet 6082 includes a first surface (not labeled), the lower sheet 6084 includes a second surface (not labeled), and the first surface opposes the second surface. The detecting element 606 is curved and is disposed on the first surface and the second surface. The upper sheet 6082 includes a number of through holes, and the lower sheet 6084 includes a number of through holes. In one embodiment according to FIG. 13, the covering structure 608 has a cube structure, and the upper sheet 6082 is substantially parallel with the lower sheet 6084.

In use, if infrared irradiates on the upper sheet 6082, because the upper sheet 6082 includes a number of through holes, the part of the detecting element 606 disposed on the first surface is able to absorb the infrared, and used as an absorbing part, and the other part of the detecting element 606 is the non-absorbing part. When the infrared irradiates on the lower sheet 6084, because the lower sheet 6084 includes a number of through holes, the part of the detecting element 606 disposed on the second surface is able to absorb the infrared and is used as an absorbing part, and the other part of the detecting element 606 is the non-absorbing part. As such, the infrared detector 60 disclosed here can detect infrared from different directions.

Other characteristics of the infrared detector 60 are the same as the infrared detector 10 disclosed above.

It is to be understood that the above-described embodiments are intended to illustrate rather than limit the present disclosure. Variations may be made to the embodiments without departing from the spirit of the disclosure as claimed. It is understood that any element of any one embodiment is considered to be disclosed to be incorporated What claimed is:

1. An infrared detector comprising:
a detecting element comprising an absorbing part, a non-absorbing part, a first end located in the absorbing part, a second end located in the non-absorbing part, and a curve that makes an angle between the absorbing part and the non-absorbing part that is less than 90 degrees;
a first electrode electrically connected with the first end; and
a second electrode electrically connected with the second end,
wherein the absorbing part extends directly from the curve along a first plane, the non-absorbing part extends directly from the curve along a second plane, the first plane and second plane are non-parallel planes, and the intersection between the first plane and the second plane shares said angle.

2. The infrared detector of claim 1, further comprising an insulated structure comprising a first surface and a second surface, wherein the first surface and the second surface lie within non-parallel planes and create an angle where they connect, and the angle between the first surface and the second surface is less than 90 degrees, the absorbing part is disposed on the first surface, and the non-absorbing part is disposed on the second surface.

3. The infrared detector of claim 2, wherein a material of the insulated structure comprises glass, ceramic, polymer, or wood.

4. The infrared detector of claim 2, further comprising a reflective layer disposed between the insulated structure and the detecting element.

5. The infrared detector of claim 4, wherein the reflective layer is an IR-reflective layer, and the reflective layer comprises a material that is selected from the group consisting of $TiO_2$—Ag—$TiO_2$, ZnS—Ag—ZnS, AlNO—Ag—AlN, $Ta_2O_3$—SiO, and $Nb_2O_3$—$SiO_2$.

6. The infrared detector of claim 1, wherein the detecting element further comprises a carbon nanotube layer comprising a plurality of carbon nanotubes disposed uniformly.

7. The infrared detector of claim 6, wherein the single-walled carbon nanotubes are oriented in a same direction and joined end-to-end by Van der Waals attractive force.

8. The infrared detector of claim 6, wherein a heat capacity per unit area of the carbon nanotube layer is less than or equal to about $2 \times 10^{-4}$ J/$cm^2$*K.

9. The infrared detector of claim 6, wherein the carbon nanotube layer is a freestanding structure.

10. The infrared detector of claim 1, wherein an area ratio between the absorbing part and the non-absorbing part is in a range from about 1:2 to about 2:1.

11. An infrared detector comprising:
a carbon nanotube layer defining an absorbing part and a non-absorbing part, a first end located in the absorbing part, a second end located in the non-absorbing part, and a curve that makes an angle between the absorbing part and the non-absorbing part that is less than 90 degrees, the carbon
nanotube layer comprises a plurality of carbon nanotube joined with each other by van der Waals attractive force;
a first electrode electrically connected with the first end; and
a second electrode electrically connected with the second end,
wherein the absorbing part extends directly from the curve along a first plane, the non-absorbing part extends directly from the curve along a second plane, the first plane and second plane are non-parallel planes, and the intersection between the first plane and the second plane shares said angle.

12. The infrared detector of claim 11, wherein the carbon nanotube layer is configured to have an incoming infrared irradiating on the absorbing part and not irradiating on the non-absorbing part.

13. The infrared detector of claim 11, further comprising an insulated structure comprising a first surface and a second surface, wherein the first surface and the second surface lie within non-parallel planes and create an angle where they connect, and the angle between the first surface and the second surface is less than 90 degrees, the absorbing part is disposed on the first surface, and the non-absorbing part is disposed on the second surface.

* * * * *